United States Patent [19]
Bailey

[11] 3,978,846
[45] Sept. 7, 1976

[54] SYRINGE FOR TAKING BLOOD SAMPLES
[76] Inventor: Donald L. Bailey, 11018 Muriel Place, Thornton, Colo. 80233
[22] Filed: Jan. 2, 1975
[21] Appl. No.: 538,101

[52] U.S. Cl. .......................... 128/2 F; 128/DIG. 5; 128/218 C; 128/218 G
[51] Int. Cl.² ............................................ A61B 5/14
[58] Field of Search ........... 128/2 F, DIG. 5, 218 R, 128/218 C, 218 G, 218 P, 218 PA, 234; 222/386

[56] References Cited
UNITED STATES PATENTS

| | | | |
|---|---|---|---|
| 1,559,978 | 11/1925 | Page | 128/218 G X |
| 1,569,457 | 1/1926 | Carstens | 128/218 G |
| 2,015,970 | 10/1935 | Schoene | 128/218 P |
| 3,146,163 | 8/1964 | Brewer | 128/DIG. 5 |
| 3,322,114 | 5/1967 | Portnoy et al. | 128/2 |
| 3,405,706 | 10/1968 | Cinqualbre | 128/DIG. 5 X |
| 3,572,556 | 3/1971 | Pogacar | 222/400.8 |
| 3,734,079 | 5/1973 | Weber | 128/218 C X |
| 3,734,080 | 5/1973 | Petterson et al. | 128/2 F |
| 3,809,298 | 5/1974 | Harris, Sr. et al. | 128/218 P X |

FOREIGN PATENTS OR APPLICATIONS

| | | | |
|---|---|---|---|
| 370,682 | 3/1923 | Germany | 128/218 G |
| 471,148 | 5/1952 | Italy | 128/218 G |

OTHER PUBLICATIONS

Introd. to Clinical Laboratory, 1966, Yearbook Med. Publ., Inc., Chicago, pp. 26–28.

*Primary Examiner*—Kyle L. Howell
*Attorney, Agent, or Firm*—Burton, Crandell & Polumbus

[57] ABSTRACT

The syringe of the present invention includes a tubular body having a plunger slidably received therein in fluid tight relationship so as to define a void space at the leading end of the syringe when the plunger is fully inserted, the void space being in communication with (1) a connector adapted to receive a hypodermic needle or the like and (2) a vent opening laterally through the side wall of the tubular body. The vent has a conduit connected thereto so that the initial flow of blood into the syringe will pass through the void space and into the conduit to purge air from the void space so that the subsequent flow of blood into the syringe will be free of air contamination. In the preferred form of the syringe, the conduit is connected to a second tubular body having a plunger therein adapted to create a low pressure zone to draw blood from the artery of a patient whose blood pressure is not sufficient to pump blood naturally into the syringe.

10 Claims, 3 Drawing Figures

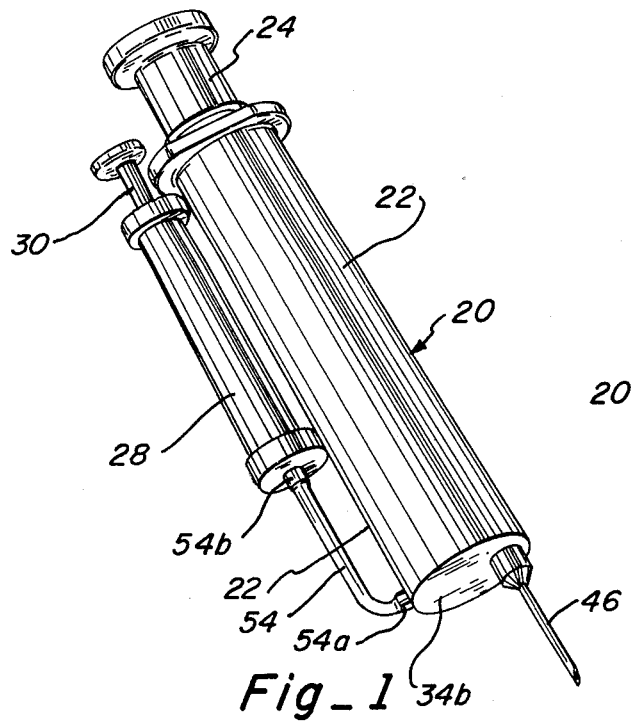
Fig_1
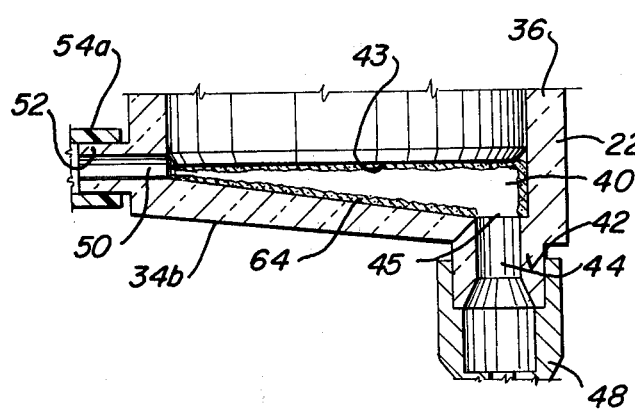
Fig_3
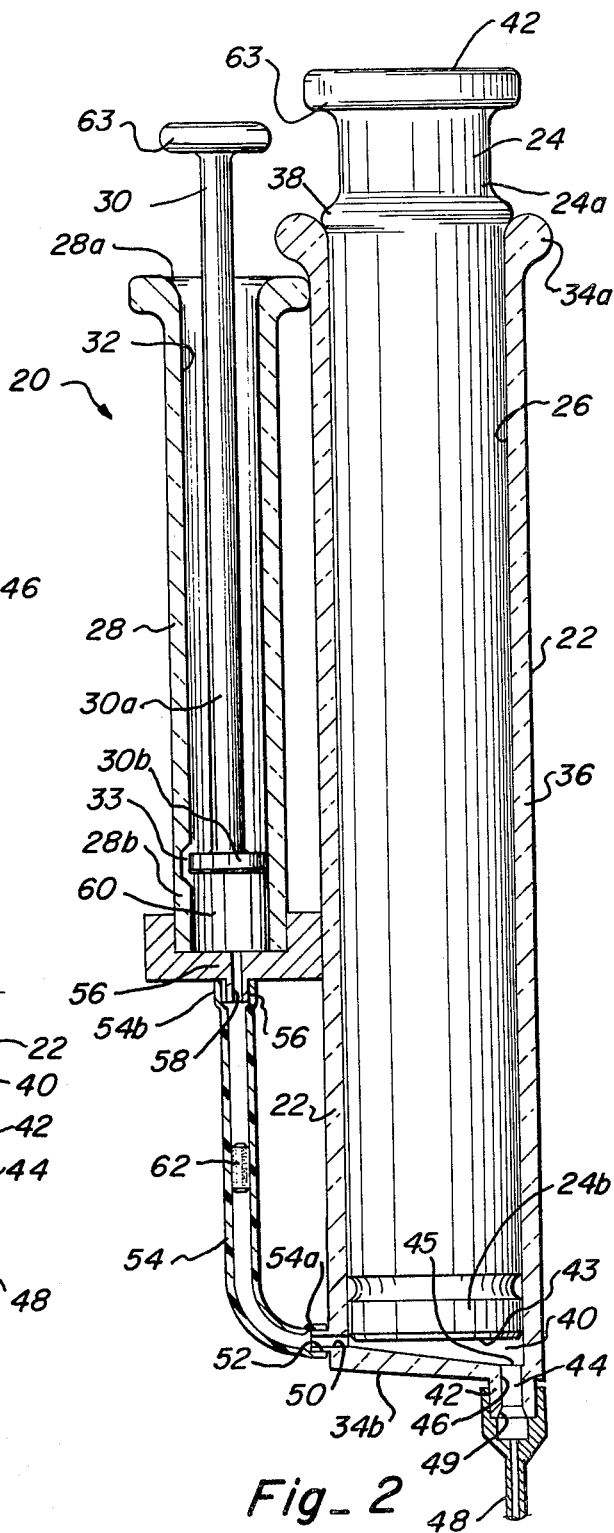
Fig_2

SYRINGE FOR TAKING BLOOD SAMPLES

BACKGROUND OF THE INVENTION

In blood gas analysis, it is important that air or other gaseous materials not be allowed to contaminate the blood as these contaminates distort the results of the gas analysis. Accordingly, prior art syringes adapted to withdraw blood samples from donors are normally preconditoned by the addition of a heparin solution to fill the void or dead space in the syringe and needle and to purge the syringe and needle of air or other gaseous materials and to provide an anticoagulant for the blood. The heparin solution, however, is typically very dilute with the heparin concentration being approximately 1000 units per milliliter and the diluent being made up of alcohol, water, and other materials which can also distort the gas analysis of the blood.

Therefore, it is desirable in taking blook samples for gas analysis to isolate the blood from extraneous gaseous materials and from the diluent of the heparin solution while leaving the heparin itself to prevent coagulation of the blood.

Accordingly, it is an object of the present invention to provide a new and improved syringe for taking blood samples which prevents contamination by extraneous gases or the diluent of a heparin solution.

It is another object of the present invention to provide a syringe for taking blood from a donor wherein the syringe has a vent opening through which air and other gaseous materials can be removed from the interior chamber of the syringe so that blood admitted into the syringe is not contaminated thereby.

It is still another object of the present invention to provide a syringe having a coating of a dry heparin material in the interior thereof to prevent the coagulation of blood drawn into the syringe and vent means for removing air from the interior chamber of the syringe so that the air does not contaminate the blood admitted to the syringe.

SUMMARY OF THE INVENTION

The syringe of the present invention includes a main tubular body which slidably receives a plunger in sealed relationship therewith. The leading end of the tubular body is closed and spaced from the leading end of the plunger when the plunger is fully inserted into the tubular body to define a minimal void space within the tubulr body at the leading end thereof to provide a pathway for fluid flow. The leading end is inclined relative to the side walls of the tubular body so that the void space is thinner on one side of the body than on the other to facilitate purging of the dead space by funneling the fluids toward the vent. A connector for a hypodermic needle or the like is provided in the leading end so as to communicate with the thicker side of the void space and a vent opening is provided through the side wall of the tubular body in communication with the thinner portion of the void space. This opposing arrangement of inlet and outlet also facilitates fluid flow by causing the blood to well up through the void space traversing the full face of the plunger without trapping air pockets as it is passes through the vent opening. A conduit is connected to the tubular body in communication with the vent opening and in the preferred form is connected with a second tubular body having a second plunger member so that a low pressure zone can be created relative to the pressure within the void space to facilitate the removal of blood from donor patients having extremely low blood pressures.

The void space in the first tubular body is coated with a dry anticoagulant by exposing the void space to a liquid anticoagulant solution and allowing the solution to evaporate to deposit the dried anticoagulant as a precipitate prior to the use of the syringe. When the needle on the syringe is inserted into the artery of the donor, the blood pressure of the donor is normally sufficient to pump the blood into the syringe where it flows through the void space in the first tubular member purging the void space of air and subsequently flows through the vent opening into the conduit which is connected to the second tubular body. The conduit is provided with a filter, one way valve, self-sealing insert or other similar device to at least restrict the forward flow of the blood in the conduit and prevent the reverse flow. When the blood is inhibited in its forward flow through the conduit, it will then begin filling the first tubular body by axially forcing the plunger member through the body to increase the space available for the blood. The blood filling the first tubular body will be free of all contaminating gases and will be exposed to the dry anticoagulant so that it will not coagulate and yet will not be adversely affected by contaminates which are normally existent in dilute solutions of anticoagulants containing alcohol, water, and other diluent materials.

BRIEF DESCRIPTION OF THE DRAWINGS

FIG. 1 is a perspective view of the syringe of the present invention.

FIG. 2 is an enlarged longitudinal section taken through the syringe of FIG. 1.

FIG. 3 is a further enlarged longitudinal section taken through the leading end of the syringe of FIG. 1.

DESCRIPTION OF THE PREFERRED EMBODIMENT

A preferred form of the syringe 20 of the present invention includes a main tubular body 22 of circular transverse cross section, a slide member or plunger 24 slidably received therein in sealed relationship with the internal walls 26 of the tubular body, an auxiliary tubular body 28 of circular transverse cross-section but of smaller diameter than the main tubular body and having a second plunger member 30 slidably received therein in sealed relationship with the internal surfaces 32 thereof.

The second plunger consists of a plunger rod 30a with a disk 30b on the low end of the rod which is in slidable sealed relationship with the internal wall of the auxiliary tubular body 28. A by-pass notch 33 is provided in the internal wall of the auxiliary body 28 and extends along the length of the body a distance which is greater than the thickness of the disc 30b so that fluids can flow through the auxiliary body when the disc on the plunger is aligned with the notch.

The main tubular body 22 has an open trailing end 34a through which the plunger 24 is inserted and a leading end wall 34b at the opposite end thereof which is inclined relative to the cylindrical side wall 36 of the main body. An annular abutment bead 38 is provided on the plunger 24 near its trailing end 24a and is adapted to abut the trailing end 34a of the main tubular body to limit the inward sliding movement of the plunger member so that a void or dead space 40 is defined between the leading end 24b of the plunger and the leading end 34b of the main tubular body. The void space varies in thickness due to the inclination of the leading end 34b of the main body so that it is thinner on one side of the body than on the other. On the side of the body where the void space is thickest, a cylindrical forward extension 42 is provided. This cylindrical extension has an axial passage 44 therethrough and communicates with a passage 46 through the leading end of the main body. The cylindrical extension 42 is adapted to receive a conventional hypodermic needle 48 or the like which slides over the extension and is sealed therewith in a conventional manner. The wall 49 at the leading end of the passage 44 is frustoconical in configuration and concentric with the longitudinal axis of the passage 44 so that blood flowing through the needle 48 and into the main body 22 is not restricted by a blunt leading end of the extension 42. The frustoconical wall 49 is convergent in a rearward direction.

A vent opening 50 is provided through the side wall of the main body 22 on the side thereof where the void space 40 is thinnest with the vent opening being situated so as to be contiguous with the leading end 24b of the plunger when the plunger is fully inserted into the main body 22. This relationship assures the removal of all gaseous material from the void space when the blood sample is initially drawn as will be explained more fully later. In the disclosed form, the diameter of the vent opening is identical to the thickness of the void space at the location where it communicates with the void space. A cylindrical protrusion 52 concentric with the vent opening 50 protrudes laterally away from the side wall 36 of the main body and receives thereon sealed relationship the leading end 54a of a conduit 54 preferably of a non-gas diffusable transparent or translucent material. The trailing end 54b of the conduit is connected to a cylindrical extension 56 from the leading end of the auxiliary tubular body 28. The cylindrical extension 56 is concentric with an opening 58 provided in the leading end of the auxiliary body 28. It will, therefore, be appreciated that the void space 40 in the main tubular body is connected by the conduit 54 to the interior 60 of the auxiliary tubular body so that when the plunger 30 in the auxiliary body is withdrawn or moved axially in a rearward direction out of the trailing open end 28a of the syringe, a low pressure zone relative to the pressure in the void space 40, can be created at the leading end 28b of the auxiliary tubular body. This relationship, while not normally important to the operation of the syringe, is useful with donors having extremely low blood pressures as will be more fully explained later.

A filter 62 is disposed in the conduit 54 and is adapted to restrict the flow of blood through the conduit toward the auxiliary tubular body 28 and prevent the reverse flow of blood back toward the main tubular body 22. This filter could be in the form of a fibrous material, a one-way valve, self-sealing insert or the like, but is preferably an absorbent material which expands upon contact with blood to substantially prevent the reverse flow of blood thereby.

The entire device is made of a sterilizable material so that it can be sterilized before use, and preferably the material is economical so that the syringe can be disposed of after use. Further, each plunger is preferably provided with an overhang 63 on its trailing end to facilitate manipulation thereof.

In operation of the syringe when dealing with patients with normal blood pressures, a dilute solution of an anticoagulant, such as heparin, is drawn into the void space 40 at the leading end 34b of the main tubular body by inserting the leaing end of the syringe into a solution of the heparin and then withdrawing the plunger 24. The solution of heparin is then allowed to evaporate leaving the dried heparin a a precipitate coating 64 (FIG. 3) on the internal walls of the main body 22 and the plunger 24. This process can be quickened by heating the syringe with the heparin solution therein at a selected temperature for a predetermined period of time. After the void space 40 has been coated with the dried heparin material, the needle 48 is attached to the extension 42 and inserted into the artery of the donor patient where the blood pressure will pump the blood through the needle, into the void space, and subsequently into the conduit 54 where the blood will initially pass into the filter 62 which restricts the flow of the blood in this direction to an extent such that the relative resistances to the blood flow between the conduit 54 and the plunger 24 in the main body 22 will allow the pressure to pump the blood into the main body. The blood will lift the plunger, or in other words, slide it axially in a reverse direction as the blood fills the internal chamber of the main tubular body. Air or other gaseous material which occupied the void space 40 in the main tubular body before the blood was pumped thereinto was purged therefrom as the blood was forced into the conduit. The blood entering the main tubular body is exposed to the dried heparin coating 64 so that it does not coagulate but the contaminating diluents which are normally existent in liquid heparin solutions are not present to contaminate the blood insofar as they affect the the blood for gas analysis. It should be noted that the disc 30b on the plunger 30 in the auxiliary body must be aligned with the notch 33 in the internal wall of the auxiliary body when the blood initially flows into the syringe to allow free flow into the conduit 54. After the blood reaches the filter 62, the plunger 30 can be moved to seal the auxiliary body to restrict further blood flow in the conduit 54.

When the syringe is used on a donor having an extremely low blood pressure, which is insufficient to pump the blood into the syringe, the needle 48 is inserted into the artery of the patient and the auxiliary plunger 30 is withdrawn to lower the pressure at the trailing end 54b of the conduit 54 so that the blood will be drawn through the needle, the void space and into the conduit where the filter 62 will restrict the forward flow and prevent the rearward flow of the blood. When the operator has observed the flow of blood into the filter, the plunger 24 in the main body is then withdrawn to draw blood from the artery of the patient into the main body until the desired sample has been drawn. Of course this sample of blood will not have extraneous gaseous material nor the diluent normally existent in solutions of heparin so that the gas analysis of the blood sample will be more accurate than has been possible with existing prior art syringes.

Although the present invention has been described with a certain degree of particularity, it is understood that the present dislosure has been made by way of example and that changes in details of structure may be made without departing from the spirit thereof.

What is claimed is:

1. In a syringe for drawing blood comprising:

a tubular body having a substantially closed leading end with open connection means at said leading end adapted for connection to a needle to be inserted into a donor's blood vessel to transfer blood from the blood vessel into the tubular body, an open trailing end, and a laterally opening passage near the leading end, a slide member slidably received in said tubular body in fluid tight relationship therewith, a void space inside the tubular body at the leading end thereof when the slide member is fully advanced into the tubular body, said slide member having a leading end and said lateral passage is disposed in the general plane of the leading end of the slide member in communication with said void space when said slide member is fully advanced, and conduit means connected to said tubular body in fluid communication with said lateral passage, said conduit means establishing means for allowing the free flow of air under arterial pressure exerted through said connection means from said tubular body through said conduit means and for preventing any air which may have been in said tubular body from contaminating a sample of blood drawn into said tubular body.

2. The syringe of claim 1 further including means operably connected to said conduit means to assist in drawing fluids into said conduit means from said tubular body.

3. The syringe of claim 2 wherein said means for drawing fluids into said conduit means includes a second tubular body having plunger means therein adapted to create a relatively low pressure zone compared to that existent in the first mentioned tubular body.

4. The syringe of Claim 3 wherein said second tubular body is positioned contiguous with said first mentioned tubular body and the tubular bodies have the longitudinal axes thereof extending parallel to each other.

5. The syringe of claim 1 wherein said leading end of the tubular body is inclined relative to the longitudinally extending walls of the tubular body to provide the void space.

6. The syringe of claim 5 wherein said void space is thinner on one side of the body than on the other and said laterally opening passage is situated so as to communicate with the thinner portion of said void space.

7. The syringe of claim 1 wherein said connection means comprises a reduced extension having a passage therethrough in communication with an opening in the leading end of the tubular body and extending parallel to the longitudinal axis of the tubular body.

8. The syringe of claim 7 wherein the leading end of said reduced extension has a frustoconical inner surface concentric with the passage therethrough, the frustoconical surface being rearwardly convergent.

9. The syringe of claim 1 further including means in said conduit means for at least partially restricting the flow of blood through said conduit means.

10. The syringe of claim 1 furher including a coating of a dried anticoagulant material on an inner surface of said tubular body to prevent coagulation of blood in the tubular body.

* * * * *